US00PP25286P2

(12) United States Plant Patent
Klemm et al.

(10) Patent No.: US PP25,286 P2
(45) Date of Patent: Feb. 10, 2015

(54) ***CALIBRACHOA* PLANT NAMED 'KLECA13252'**

(50) Latin Name: ***Calibrachoa* sp.**
Varietal Denomination: KLECA13252

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 58 days.

(21) Appl. No.: 13/987,413

(22) Filed: Jul. 23, 2013

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Kent L Bell
(74) *Attorney, Agent, or Firm* — Barbara Campbell; Cochran Freund & Young LLC

(57) ABSTRACT

A new *Calibrachoa* plant particularly distinguished by having red-purple flowers and a semi-upright plant habit, is disclosed.

1 Drawing Sheet

Genus and species: *Calibrachoa* sp.
Variety denomination: 'KLECA13252'.

BACKGROUND OF THE NEW PLANT

The present invention comprises a new and distinct variety of *Calibrachoa*, botanically known as *Calibrachoa* sp., and hereinafter referred to by the variety name 'KLECA13252'. 'KLECA13252' originated from a controlled cross between the female *Calibrachoa* variety 'KLECA08178' (U.S. Plant Pat. No. 21,060) and the male *Calibrachoa* variety 'KLECA06124' (U.S. Plant Pat. No. 19,476) in May 2009.

In May 2009, seed was collected from the controlled cross between the two *Calibrachoa* parental lines, 'KLECA08178' and 'KLECA06124' in Stuttgart, Germany. The seeds were sown and plants were grown for evaluation. A single plant line was selected in May 2010 which had red-purple flowers and was subsequently named 'KLECA13252'. In May 2010, 'KLECA13252' was first vegetatively propagated by tip cuttings. 'KLECA13252' was found to reproduce true to type in successive generations of asexual propagation via tip cuttings.

CROSS REFERENCE TO RELATED APPLICATION

Plant Breeder's Rights for 'KLECA13252' were applied for in Canada on January 23, 2013, Application No. 13-7854. 'KLECA13252' has not been made publicly available or sold more than one year prior to the filing date of this application.

SUMMARY

The following are the most outstanding and distinguishing characteristics of this new variety when grown under normal horticultural practices in Stuttgart, Germany.

1. Red-purple flowers; and
2. A semi-upright plant habit.

DESCRIPTION OF THE PHOTOGRAPH

This new *Calibrachoa* plant is illustrated by the accompanying photograph which shows the foliage, buds, and a closeup of the flowers. The photograph is of a five-month-old plant grown in Stuttgart, Germany in May 2012. The colors shown are as true as can be reasonably obtained by conventional photographic procedures.

DESCRIPTION OF THE NEW VARIETY

The following detailed descriptions set forth the distinctive characteristics of 'KLECA13252'. The data which define these characteristics were collected from asexual reproductions carried out in Stuttgart, Germany. Data was collected on 5-month-old plants grown in a controlled greenhouse environment in Stuttgart, Germany in May 2013. Color references are to The R.H.S. Colour Chart of The Royal Horticultural Society of London (R.H.S.) (2007).

Classification:
- *Family.*—Solanaceae.
- *Botanical.*—*Calibrachoa* sp.
- *Common.*—*Calibrachoa.*
- *Designation.*—'KLECA13252'.

Parentage:
- *Female parent.*—*Calibrachoa* line 'KLECA08178' (U.S. Plant Pat. No. 21,060).
- *Male parent.*—*Calibrachoa* line 'KLECA06124' (U.S. Plant Pat. No. 19,476).

Plant:
- *Life cycle.*—Annual.
- *Form and habit.*—Semi-upright.
- *Height (from soil line to top of foliage).*—12.0 cm.
- *Spread.*—26.0 cm.
- *Propagation.*—Vegetatively propagated by tip cuttings.
- *Time to produce a rooted cutting.*—3 weeks.

Stems:
- *Stem color.*—RHS 144A.
- *Pubescence.*—Little.
- *Pubescence color.*—RHS 144C.
- *Diameter.*—6.0 cm.
- *Length, from soil line to first node.*—1.6 cm.
- *Total length.*—15.0 cm (measured from top of the stem to the base of the apical branch)
- *Internode length.*—1.8 cm. .

Leaves:
*Arrangement*.—Alternate, simple, and sessile.
*Shape*.—Elliptic.
*Apex*.—Obtuse to slightly acute.
*Base*.—Attentuate.
*Margin*.—Entire.
*Surface*.—Smooth.
*Surface pubescence*.—Absent.
*Venation*.—Pinnate.
*Venation color*.—Upper surface: RHS 145B. Lower surface: RHS 145A.
*Length*.—2.2 cm.
*Width*.—0.9 cm.
*Color*.—Upper surface: RHS 144A. Lower surface: RHS 143C.
*Fragrance*.—Absent.

Flowers:
*Flowering habit*.—Flower attitude erect, single, and axillary.
*Flower type*.—Determinate inflorescence.
*Flowering requirements*.—A minimum of light sun is required.
*Duration of flowers*.—4 days.
*Corolla*.—Smooth texture.
*Shape*.—Funnel-shaped.
*Fragrance*.—Absent.

Flower buds:
*Surface texture*.—Smooth.
*Length*.—1.9 cm.
*Diameter*.—0.5 cm.
*Shape*.—Irregular to oblong.
*Color*.—RHS 187A.

Peduncle:
*Length*.—1.0 cm.
*Diameter*.—0.1 cm.
*Color*.—RHS 144A.
*Texture*.—Smooth.
*Anthocyanin color*.—RHS N187A.

Flower description:
*Flower depth*.—2.8 cm.
*Flower tube length*.—1.7 cm.
*Flower tube diameter*.—1.0 cm.
*Flower diameter*.—4.0 cm.
*Pedicel color*.—RHS 144A.
*Calyx*.—Funnel-shaped.

Sepals:
*Shape*.—Lanceolate.
*Apex*.—Acute.
*Margin*.—Entire.
*Length*.—1.2 cm.
*Diameter*.—0.3 cm.
*Sepal color*.—Upper surface: RHS 144A. Lower surface: RHS 144A and RHS 187A.

Petals:
*Shape*.—Heart-shaped.
*Length*.—1.7 cm.
*Apex*.—Obverse.
*Margin*.—Entire, weak undulation.
*Base*.—Open and fused into the tube.
*Pubescence*.—Absent.
*Lobe length*.—1.7 cm.
*Lobe width*.—1.7 cm.
*Lobe color*.—Upper surface: RHS N74A. Lower surface: RHS 70B.
*Corolla tube color*.—Inner: RHS 162A. Outer: RHS 162B and RHS 187A.
*Fragrance*.—Absent.

Reproductive organs:
*Stamen number*.—5.
*Stamen color*.—Anther color: RHS 163A. Filament color: RHS 163D. Pollen color: RHS 163A.
*Ovary*.—Placenta arrangement: Ovate. Pistil number: 1. Pistil length: 0.1 cm. Stigma color: RHS 154A. Style length: 0.8 cm. Style color: RHS 149B.

Fruit and seed set: Little seed production.

Disease and pest/insect resistance: None observed.

COMPARISON WITH PARENTAL LINES AND KNOWN VARIETY

'KLECA13252' is distinguished from the female and male parental lines as described in Table 1.

TABLE 1

Comparison with Parental Lines

| Trait | 'KLECA13252' | Female parent 'KLECA08178' | Male Parent 'KLECA06124' |
|---|---|---|---|
| Flower color | RHS N74A | RHS 86A | RHS 19A and RHS 45A |

'KLECA13252' is most similar to the *Calibrachoa* plant named 'KLECA05101' (U.S. Plant Pat. No. 18,610). Differences between the two varieties are described in Table 2.

TABLE 2

Comparison with Similar Variety

| Trait | 'KLECA13252' | 'KLECA05101' |
|---|---|---|
| Earliness to flower | Early; in average 10 days earlier than 'KLECA05101' | Late to medium |

We claim:

1. A new and distinct variety of *Calibrachoa* plant named 'KLECA13252' as illustrated and described herein.

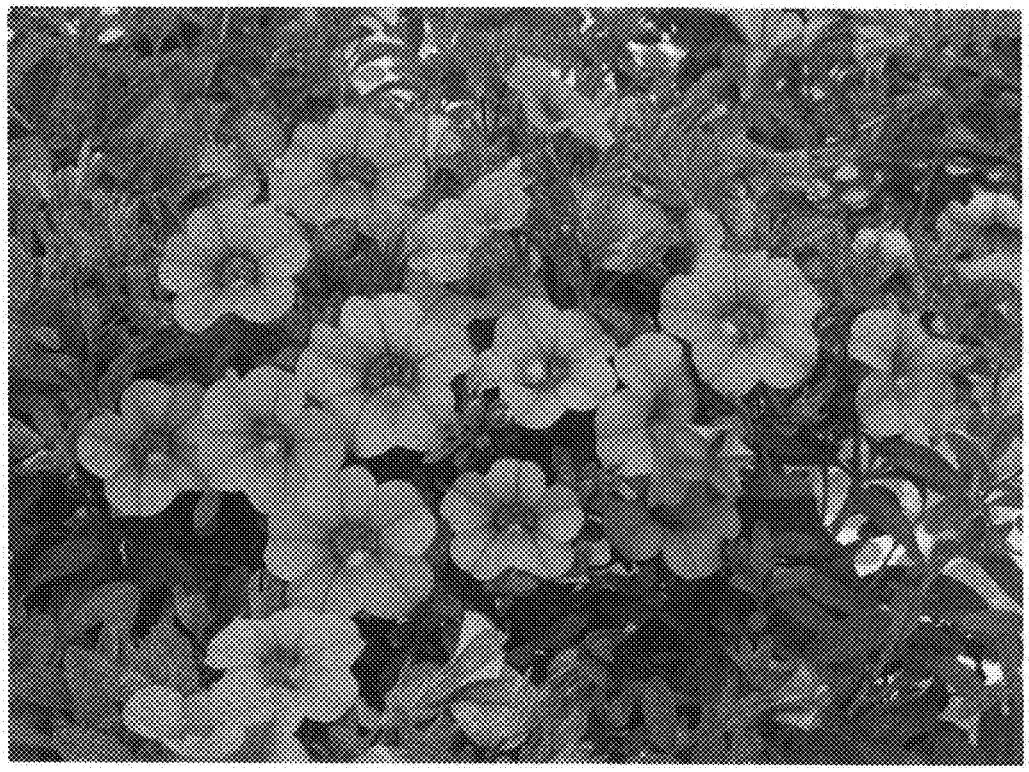

* * * * *